(12) United States Patent
Jou et al.

(10) Patent No.: US 9,346,756 B2
(45) Date of Patent: May 24, 2016

(54) ELECTRO-FLUORESCENT EMITTER FOR ULTRA-VIOLET OLED

(71) Applicant: National Tsing Hua University, Hsinchu (TW)

(72) Inventors: Jwo-Huei Jou, Hsinchu (TW); Sudhir Kumar, Hsinchu (TW); Justin Thomas Koil Pitchai Rajapandian, Hsinchu (TW)

(73) Assignee: National Tsing Hua University (TW)

( * ) Notice: Subject to any disclaimer, the term of this patent is extended or adjusted under 35 U.S.C. 154(b) by 0 days.

(21) Appl. No.: 14/522,749

(22) Filed: Oct. 24, 2014

(65) Prior Publication Data

US 2016/0115127 A1    Apr. 28, 2016

(51) Int. Cl.
*C07D 209/86* (2006.01)
*C07D 209/90* (2006.01)
*C09K 11/06* (2006.01)

(52) U.S. Cl.
CPC .............. *C07D 209/90* (2013.01); *C09K 11/06* (2013.01); *C07D 209/86* (2013.01); *C09K 2211/1007* (2013.01); *C09K 2211/1033* (2013.01)

(58) Field of Classification Search
CPC ........ C07D 209/86; C08F 26/12; G03G 5/07; C07C 1/323; C07C 15/14
USPC ........................................................ 548/445
See application file for complete search history.

(56) References Cited

U.S. PATENT DOCUMENTS

2012/0264649 A1* 10/2012 Bazan ..................... H01M 8/16
                                                                506/15

OTHER PUBLICATIONS

Lin, C., Y. Chang, C. Li, C. Liu, and J. Duan "Bis(arylquinoxalinyl)carbazole derivatives as saturated blue emitters for electroluminescent devices" Synthetic Metals (2006), 156: pp. 671-676.*

Iraqi, A., and I. Wataru "3,6-Linked 9-Alkyl-9H-carbazole Main-Chain Polymers: Preparation and Properties" University of Sheffield (2004), pp. 6041-6051.*

* cited by examiner

*Primary Examiner* — Alicia L Otton
*Assistant Examiner* — Sagar Patel

(57) ABSTRACT

The present invention demonstrates a newly designed and synthesized carbazole scaffold based electro-fluorescent emitter, 9-butyl-2,7-(2-(4-methoxyphenyl)ethynyl)-9H-carbazole (Cz(APhOMe)$_2$), for ultra-violet OLED. This novel emitter has showed a high quantum yield of ~78%. By doping in a host light-emitting layer of an OLED, the Cz(APhOMe)$_2$ guest light-emitting material shows a UV light belong to the near-UV region with high external quantum efficiency. Most importantly, a variety of experiment results have proved that this UV light is a pure UV light having only one peak wavelength in the emission spectrum thereof. Ascertainably, this pure UV light can be applied in numerous applications, such as biological sensors chemical sensors, leakage detection in automobiles, crack detection in airplanes, high density information storage devices, water treatment for germicidal protection, forensic investigations, sanitation and sterilization, laboratory researches, food industries, and fraud detection.

5 Claims, 14 Drawing Sheets

Table 1

| Compound | $T_d$ (°C) | HOMO (eV) | LUMO (eV) | $E_g$ (eV) | $E_{1/2,}^{Ox}$ (V) | $\lambda_{abs.}$ (nm) | $\lambda_{em.}$ (nm) |
|---|---|---|---|---|---|---|---|
| CZ(APhOMe)$_2$-A | 411 | -5.53 | -2.30 | 3.23 | 0.73 | 353, 292, 267 | 431, 388 |
| CZ(APhOMe)$_2$-B | 415 | -5.41 | -2.03 | 3.38 | 0.61 | 316, 302, 266 | 403, 380 |

FIG. 5

Table 2

| Dopant | Host | Doping Conc. (wt%) | OV (V) | EQE (%) | CIE Coordinates | $EL_{max}$ (nm) |
|---|---|---|---|---|---|---|
| | | | | | @ max./ 10 mA/cm² | |
| Cz(APhOMe)₂ | CBP | 0.5 | 4.6/- | 2.7/- | (0.161, 0.032)/- | 396 |
| | | 0.7 | 4.4/4.7 | 3.5/3.4 | (0.161, 0.032)/(0.161, 0.034) | 396 |
| | | 1 | 4.2/4.6 | 4.2/3.9 | (0.160, 0.032)/(0.160, 0.033) | 396 |
| | | 3 | 4.3/4.8 | 3.8/3.4 | (0.160, 0.038)/(0.161, 0.039) | 396 |
| | | 5 | 4.3/4.7 | 3.1/2.9 | (0.159, 0.039)/(0.160, 0.040) | 396 |
| | | 7 | 4.4/4.8 | 2.3/2.2 | (0.159, 0.045)/(0.160, 0.048) | 396 |
| | m-CBP | 0.5 | 4.3/4.7 | 2.0/2.0 | (0.161, 0.032)/(0.161, 0.034) | 392 |
| | | 0.7 | 4.4/4.9 | 2.7/2.7 | (0.160, 0.034)/(0.161, 0.040) | 392 |
| | | 1 | 4.4/5.2 | 3.0/2.7 | (0.160, 0.057)/(0.162, 0.058) | 392 |
| | | 3 | 5.0/5.1 | 3.2/3.0 | (0.160, 0.053)/(0.161, 0.054) | 396 |
| | | 5 | 4.3/4.7 | 3.1/2.8 | (0.160, 0.037)/(0.160, 0.039) | 396 |
| | | 7 | 4.5/4.6 | 2.4/2.3 | (0.158, 0.044)/(0.159, 0.046) | 396 |

FIG. 10

ELECTRO-FLUORESCENT EMITTER FOR ULTRA-VIOLET OLED

BACKGROUND OF THE INVENTION

1. Field of the Invention

The present invention relates to the technology field of OLEDs, and more particularly to an electro-fluorescent emitter for ultra-violet OLED.

2. Description of the Prior Art

Ultraviolet light, invisible to the naked eye, is one component of the natural light (i.e., sunlight). As the spectrum diagram of sunlight presented by FIG. 1 shows, the wavelength of ultraviolet light ranges between 100 nm and 400 nm. Moreover, the ultraviolet light can be further divided to Vacuum UV (VUV), Far-UV (UVC), Mid-UV (UVB), and Near-UV (UVA) with the wavelength difference of UV light. Nowadays, UV light is well known can be applied to the following technique fields: biological and chemical sensors, leakage detection in automobiles, high density information storage devices, water treatment for germicidal protection, crack detection in airplanes, forensic investigations, sanitation and sterilization, laboratory researches, food industries, and fraud detection.

Conventionally, UV light can be produced or emitted from a xenon arc lamp, an incandescent lamp, a fluorescent lamp, a mercury vapor lamp, a laser diode, or a light emitting diode (LED); that means all the xenon arc lamp, the incandescent lamp, the fluorescent lamp, the mercury vapor lamp, the laser diode, and the light emitting diode (LED) can be used as a UV light source. Please refer to FIG. 2 and FIG. 3, which illustrate the emission spectrum diagrams of two UV lights emitted by a laser diode and an LED, respectively. As FIG. 2 shows, the UV light emitted by the laser diode obviously includes a visible light component. Similarly, the UV light emitted by the LED apparently includes a visible light component as shown in FIG. 3. Moreover, according to researches, it can be known that the UV light emitted by the xenon arc lamp, the incandescent lamp, the fluorescent lamp, or the mercury vapor lamp also includes the visible light component and/or an infrared ray component.

So that, the emission spectrum diagrams have proved that the UV light emitted by the conventional UV light source is not a pure UV light. So that, it can reasonably assume that such impure UV light cannot provide a best and most-effective assistance in the technique fields of water treatment for germicidal protection, forensic investigations, sanitation and sterilization, food industries, and fraud detection; more negatively and seriously, such impure UV light may provide an adverse effect.

Organic light emitting device (OLED), a novel light device, is well known including the advantages of high brightness, fast response time, light weight, compactness, true color, no difference in viewing angles, capable of light by plane, and low power consumption. However, there is no UV OLED being proposed or fabricated up to now.

Accordingly, in view of there is still no UV OLED being proposed or fabricated, the inventor of the present application has made great efforts to make inventive research thereon and eventually provided an electro-fluorescent emitter for ultra-violet OLED.

SUMMARY OF THE INVENTION

The primary objective of the present invention is to provide an electro-fluorescent emitter for ultra-violet (UV) organic light emitting diode (OLED), wherein the electro-fluorescent emitter is a ultra-violet fluorescent emitting material performs a high quantum yield of ~78%, and can be doped into a host light-emitting layer of an OLED for being a guest light-emitting material, so as to facilitate the OLED be able to emit a UV light belong to the near-UV region with a high external quantum efficiency. Most importantly, a variety of experiment results have proved that this UV light is a pure UV light having only one peak wavelength in the emission spectrum thereof. So that, ascertainably, this pure UV light can be applied in the technique fields of biological and chemical sensors, leakage detection in automobiles, high density information storage devices, water treatment for germicidal protection, crack detection in airplanes, forensic investigations, sanitation and sterilization, laboratory researches, food industries, and fraud detection.

Accordingly, in order to achieve the primary objective of the present invention, the inventor of the present invention provides an electro-fluorescent emitter for ultra-violet OLED, and the electro-fluorescent emitter is a ultra-violet fluorescent emitting material formed by completing a Sonogashira coupling reaction of at least one polycyclic aromatic hydrocarbons (PAHs) and at least one benzene derivative.

According to one embodiment of the novel light-emitting material, wherein the PAHs is represented by following chemical formula 1 or chemical formula 2:

[chemical formula 1]

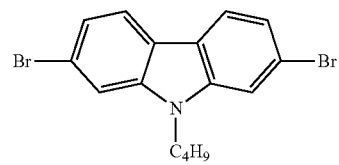

[chemical formula 2]

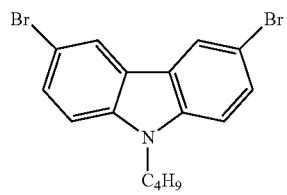

According to one embodiment of the novel light-emitting material, wherein the benzene derivative is represented by following chemical formula 3:

[chemical formula 3]

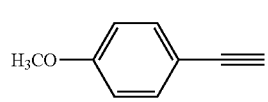

According to one embodiment of the novel light-emitting material, wherein the chemical structure of the formed ultra-violet fluorescent emitting material is represented by following chemical formula 4 or chemical formula 5:

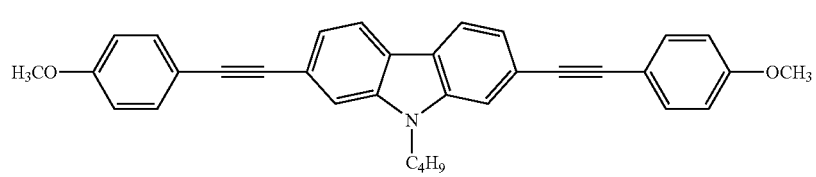

[chemical formula 4]

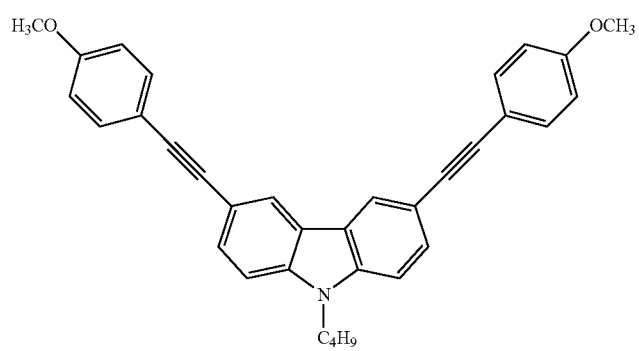

[chemical formula 5]

BRIEF DESCRIPTION OF THE DRAWINGS

The invention as well as a preferred mode of use and advantages thereof will be best understood by referring to the following detailed description of an illustrative embodiment in conjunction with the accompanying drawings, wherein:

FIG. 5 is a diagram of table 1;

FIG. 10 is a diagram of table 2;

DETAILED DESCRIPTION OF THE PREFERRED EMBODIMENTS

To more clearly describe an electro-fluorescent emitter for ultra-violet OLED according to the present invention, embodiments of the present invention will be described in detail with reference to the attached drawings hereinafter.

Figure 4A:
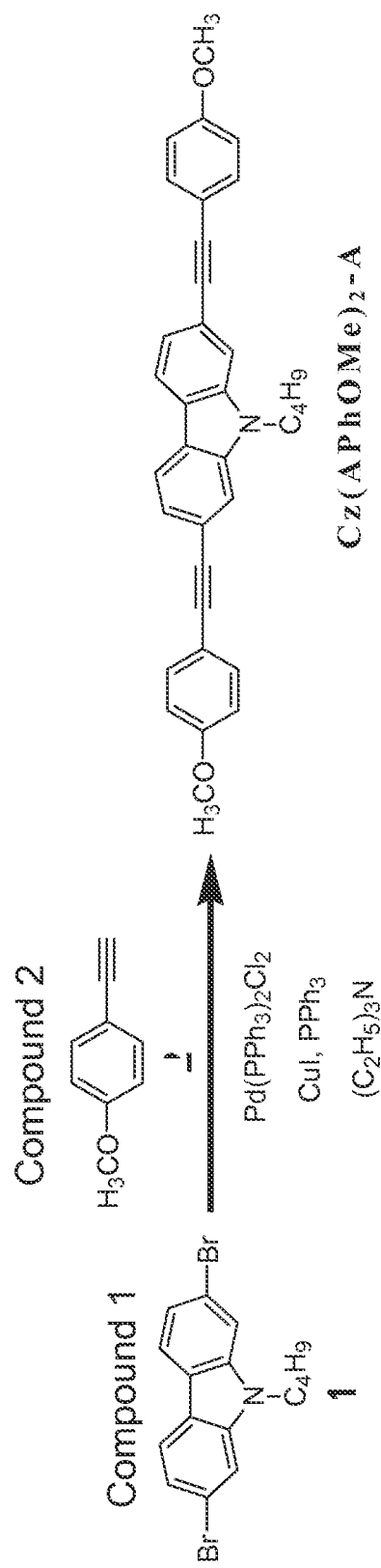
FIGS. 4A and 4B are two schematic diagrams of Sonogashira coupling reaction.
Figure 4B:
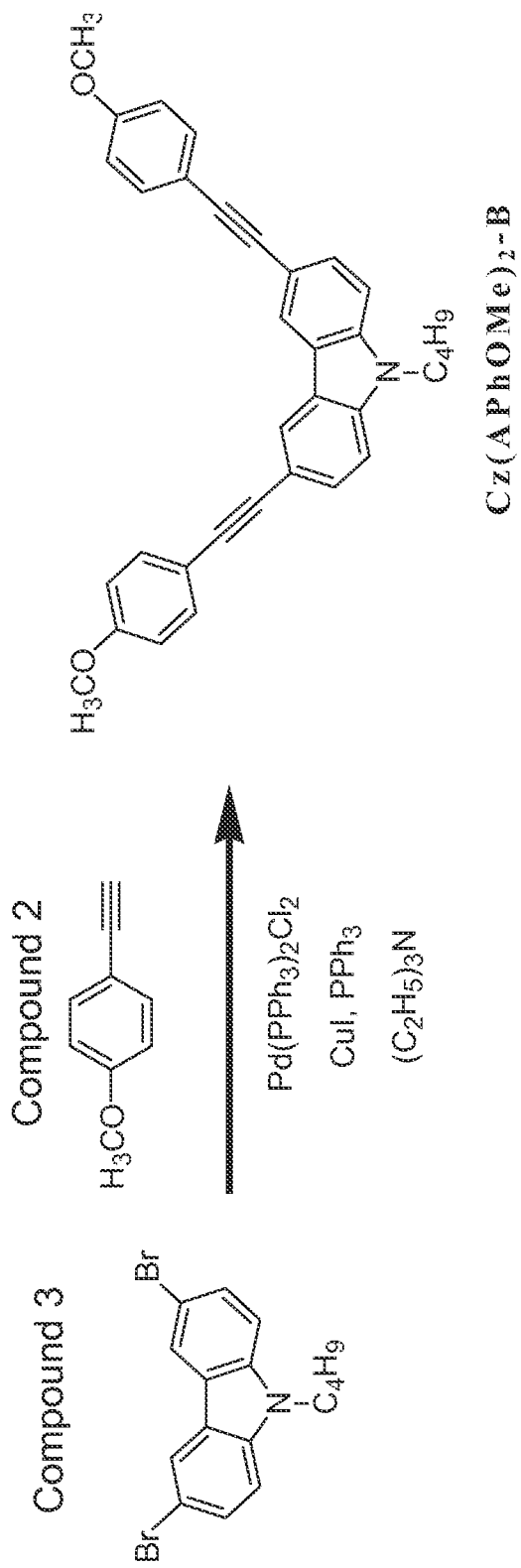

Please refer to FIG. 4A and FIG. 4B, which illustrate the schematic diagram of a Sonogashira coupling reaction. As shown in FIG. 4A and FIG. 4B, the electro-fluorescent emitter for ultra-violet OLED provided by the present invention is a ultra-violet fluorescent emitting material formed by completing a Sonogashira coupling reaction of at least one polycyclic aromatic hydrocarbons (PAHs) and at least one benzene derivative; wherein the PAHs can be the COMPOUND 1 or the COMPOUND 3 and the benzene derivative is the COMPOUND 2 shown in FIG. 4A and FIG. 4B. Moreover, in the Sonogashira coupling reaction, there are a plurality of catalytic agents be adopted, including Pd(PPh$_3$)$_2$Cl$_2$) (Palladium(II)bis(triphenylphosphine)dichloride), PPh$_3$ (Triphenylphosphine), CuI (Cuprous iodide), and (C$_2$H$_5$)$_3$N (Triethylamine).

Continuously referring to FIG. 4A and FIG. 4B, the aforesaid polycyclic aromatic hydrocarbons is represented by following chemical formula 1 or chemical formula 2:

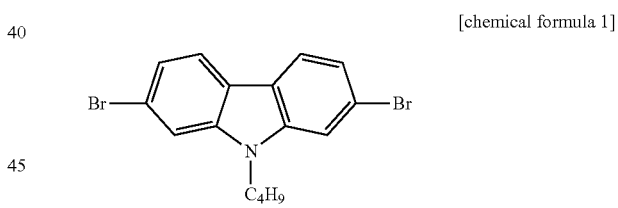

[chemical formula 1]

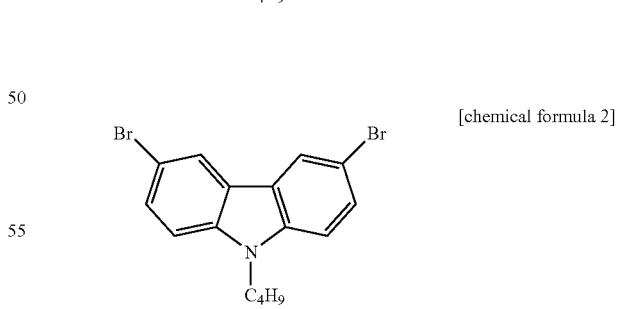

[chemical formula 2]

From the above two chemical formulas, it is able to know that the chemical formula 1 represents the chemical structure of 2,7-dibromo-9-butyl-9H-carbazole, and the chemical formula 2 represents the chemical structure of 3,6-dibromo-9-butyl-9H-carbazole. Opposite to the PAHs, the chemical structure of the benzene derivative is represented by following chemical formula 3 representing the chemical structure of 1-ethynyl-4-methoxy-benzene.

[chemical formula 3]

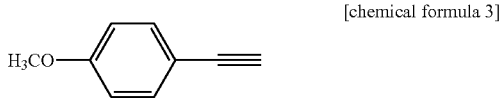

Figure 1:
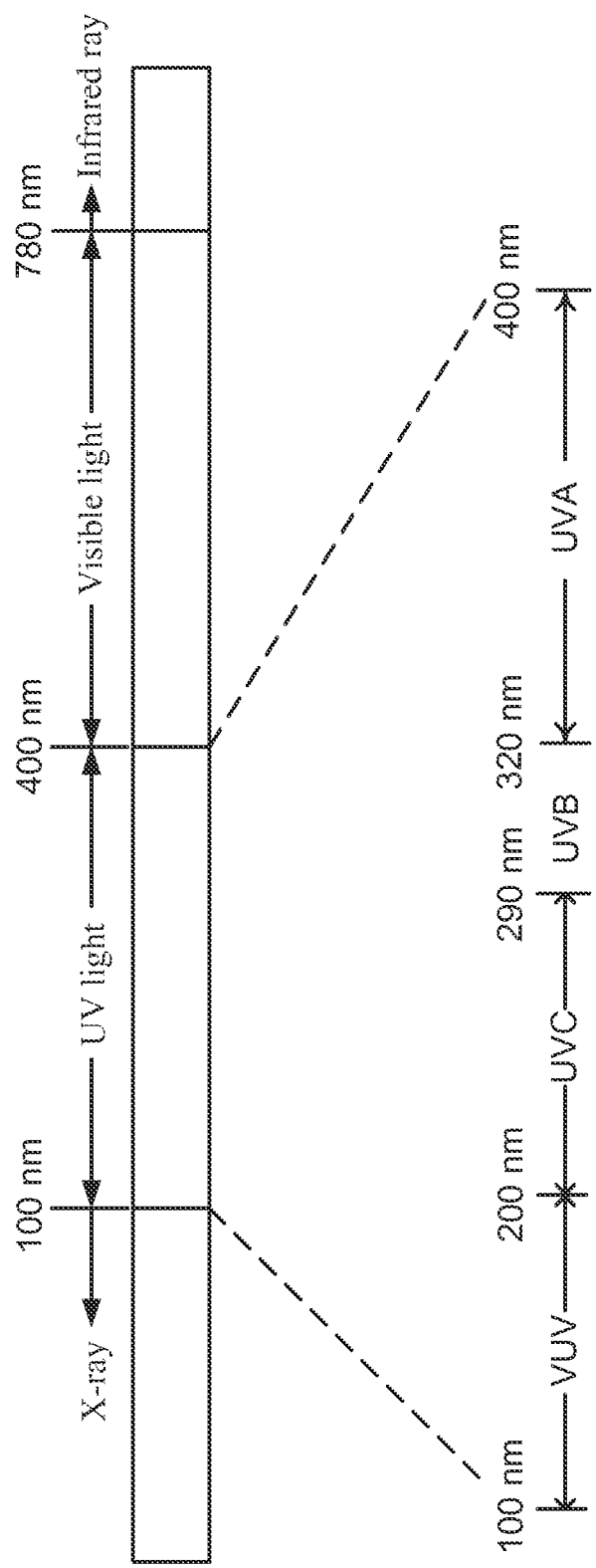
FIG. 1 is a spectrum diagram of natural light (sunlight)
Figure 2:
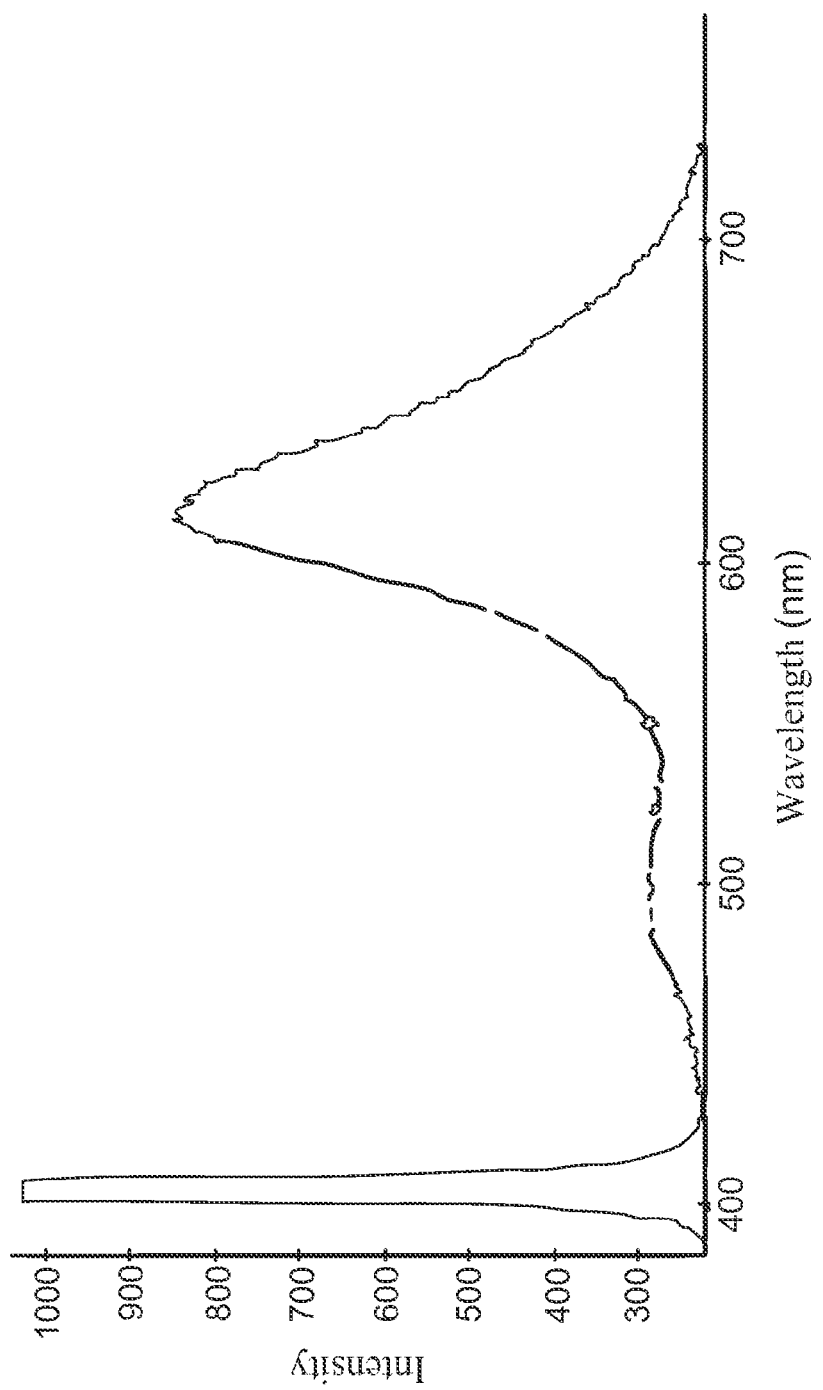
FIG. 2 is an emission spectrum diagram of a laser diode.
Figure 3:
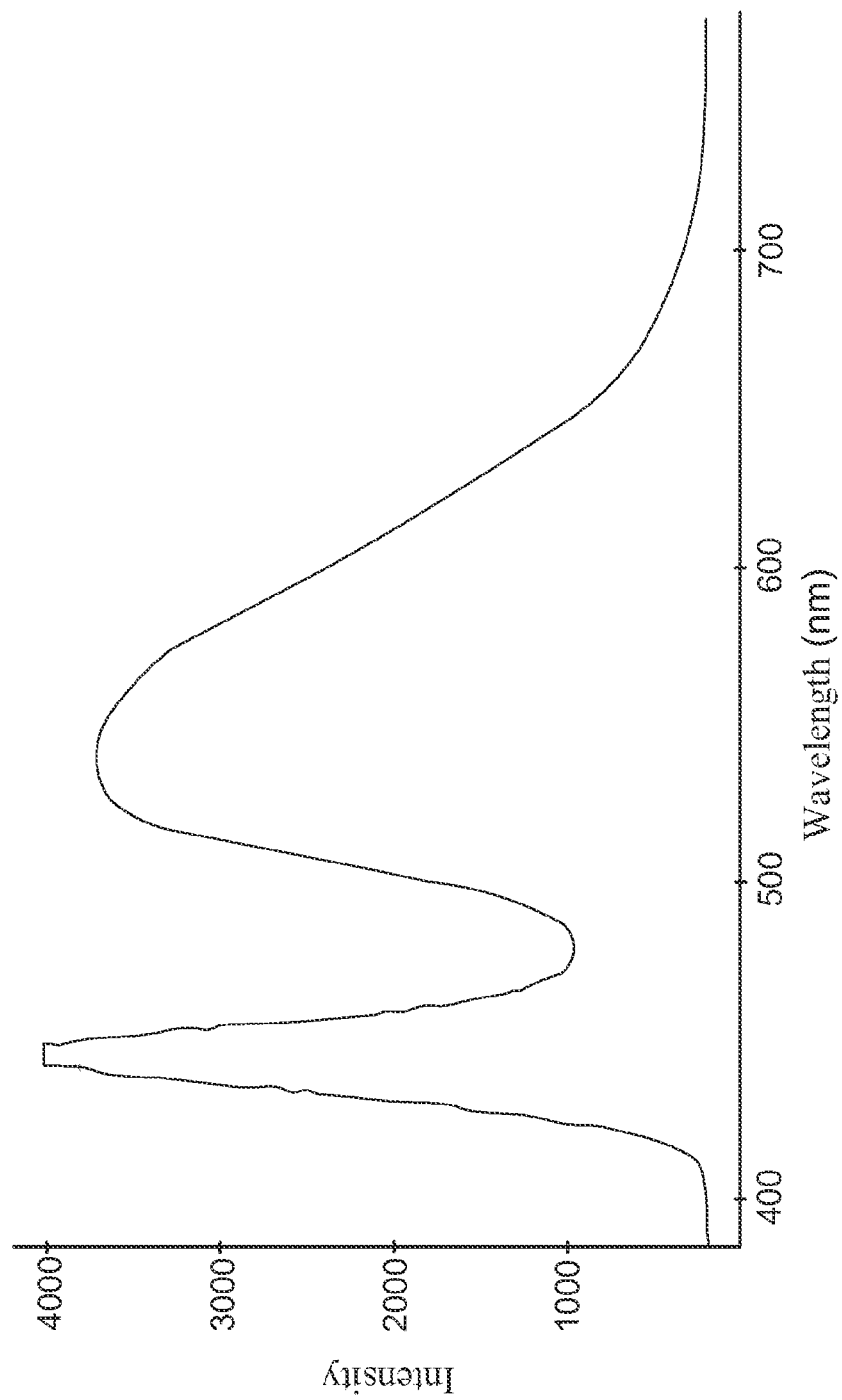
FIG. 3 is an emission spectrum diagram of a light emitting diode.

Referring to FIG. 2 again, after finishing the Sonogashira coupling reaction, the PAHs and the benzene derivative are synthesized to a ultra-violet fluorescent emitting material capable of being doped into a host light-emitting layer of an organic light emitting diode (OLED) for being a guest light-emitting material, wherein the chemical structure of the formed ultra-violet fluorescent emitting material is represented by following chemical formula 4 or chemical formula 5:

[chemical formula 4]

[chemical formula 5]

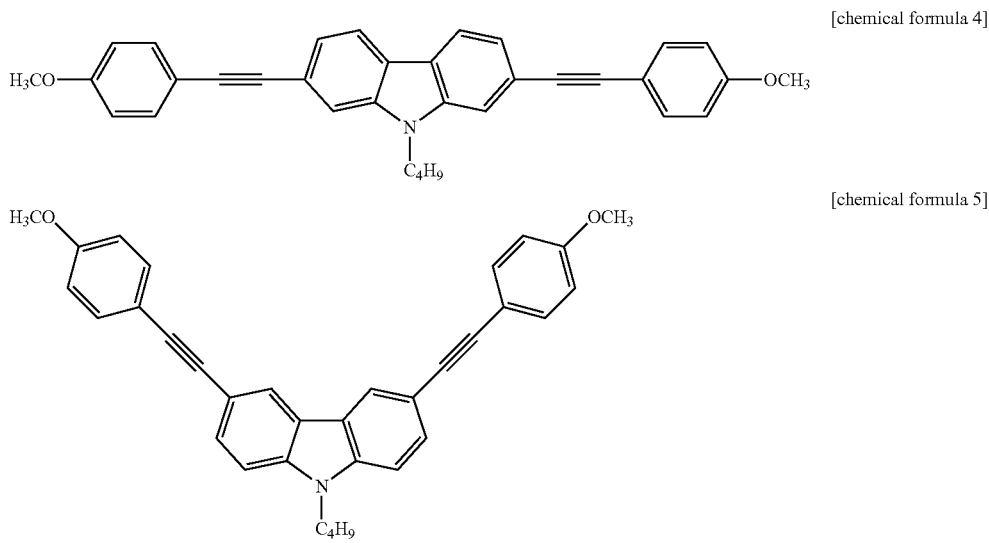

Both the above-presented chemical formula 4 represents the chemical structure of 9-butyl-2,7-(2-(4-methoxyphenyl) ethynyl)-9H-carbazole abbreviated to Cz(APhOMe)$_2$-A, and the chemical formula 5 represents the chemical structure of 9-butyl-3,6-(2-(4-methoxyphenyl)ethynyl)-9H-carbazole Cz(APhOMe)$_2$-B. Next, please refer to FIG. 5, which illustrates the diagram of table 1. From table 1, it is able to know that the ultra-violet fluorescent emitting material of Cz(APhOMe)$_2$-A has a high occupied molecular orbital energy level ($E_{HOMO}$) of −5.53 eV and a lowest unoccupied molecular orbital energy level ($E_{LUMO}$) of −2.30 eV. In addition, the peak wavelength of the absorption spectrum ($\lambda_{abs}$) of Cz(APhOMe)$_2$-A is 352 nm, 292 nm and 267 nm. Moreover, the peak wavelength of the emission spectrum ($\lambda_{em}$) of Cz(APhOMe)$_2$-A is 413 nm and 388 nm. Herein, it needs to further explain that "$T_d$" written in table 1 represent decomposition temperature of the material.

Opposite to Cz(APhOMe)$_2$-A, the ultra-violet fluorescent emitting material of Cz(APhOMe)$_2$-B has a high occupied molecular orbital energy level ($E_{HOMO}$) of −5.41 eV and a lowest unoccupied molecular orbital energy level ($E_{LUMO}$) of −2.03 eV. In addition, the peak wavelength of the absorption spectrum ($\lambda_{abs}$) of Cz(APhOMe)$_2$-B is 316 nm, 302 nm and 266 nm. Moreover, the peak wavelength of the emission spectrum ($\lambda_{em}$) of Cz(APhOMe)$_2$-B is 403 nm and 380 nm.

Figure 6A:
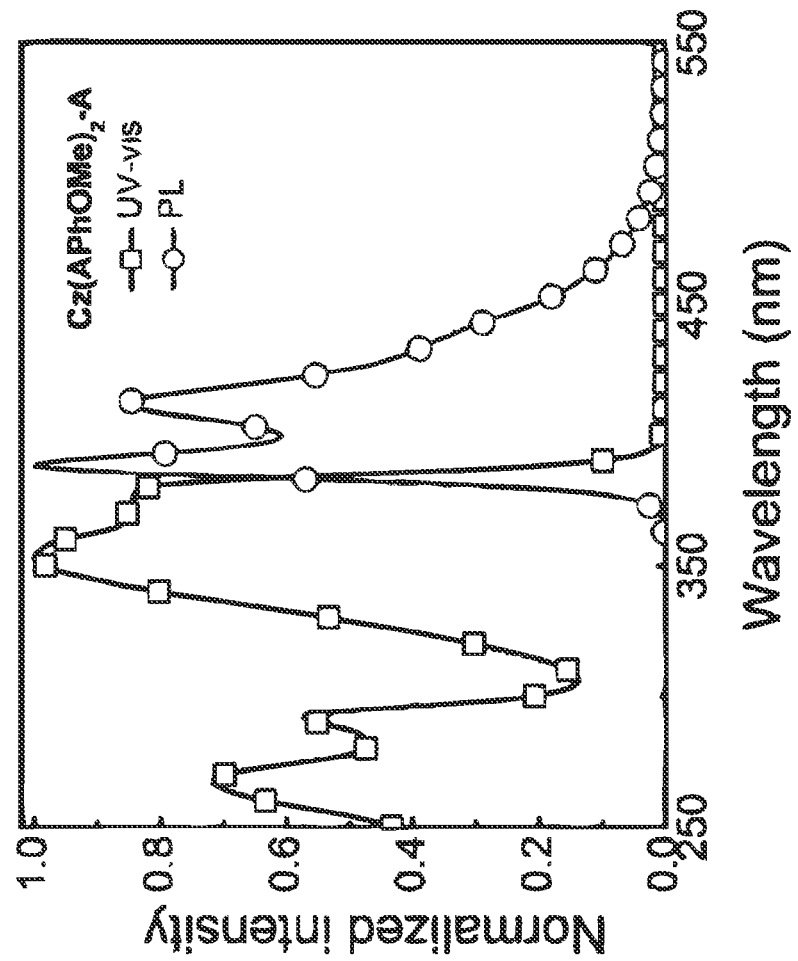
FIG. 6A is a photoluminescence spectrum diagram of a ultra-violet fluorescent emitting material of Cz(APhOMe)$_2$-A.
Figure 6B:
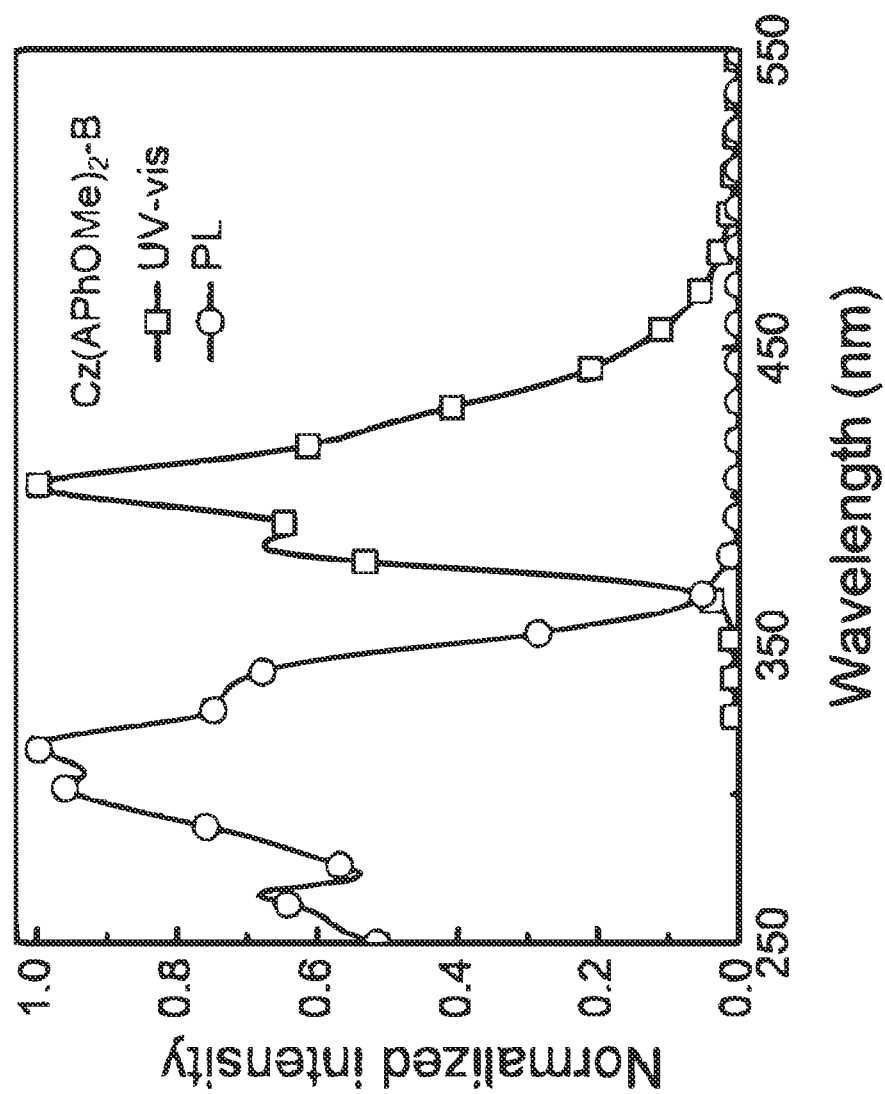
FIG. 6B is a photoluminescence spectrum diagram of a ultra-violet fluorescent emitting material of Cz(APhOMe)$_2$-B.

FIG. 6A shows a photoluminescence spectrum diagram of the ultra-violet fluorescent emitting material of Cz(APhOMe)$_2$-A. In FIG. 6A, the data curve marked with UV-vis means the ultraviolet-visible absorption spectra. Moreover, the peak wavelength of the Cz(APhOMe)$_2$-A can be found to 390 nm from FIG. 6A. Also, FIG. 6B shows a photoluminescence spectrum diagram of the ultra-violet fluorescent emitting material of Cz(APhOMe)$_2$-B. From FIG. 6B, the peak wavelength of the Cz(APhOMe)$_2$-B can be found to about 390 nm. So that, it is able to know that the UV light emitted by the ultra-violet fluorescent emitting material of Cz(APhOMe)$_2$-A or Cz(APhOMe)$_2$-B belongs to UVA (i.e., near-UV).

Figure 7:
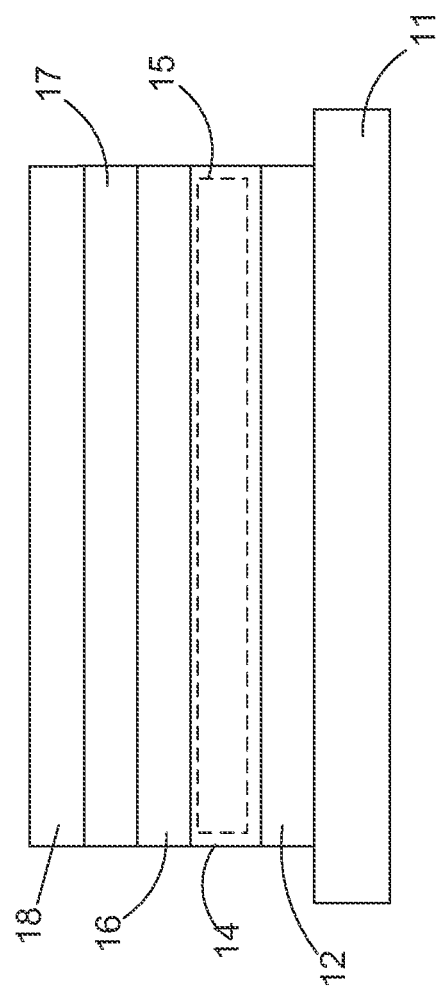
FIG. 7 is a structure diagram of an experimental organic light emitting diode (OLED)

Subsequently, a variety of experimental data will be provided for proving that the ultra-violet fluorescent emitting material of Cz(APhOMe)$_2$-A can indeed be used as a guest light-emitting material of an organic light emitting diode (OLED). Please refer to FIG. 7, which illustrate a structure diagram of an experimental organic light emitting diode (OLED). As shown in FIG. 7, the OLED 1 consists of: an anode 11, a hole injection layer 12, a host light-emitting layer 14, a guest dye 15, an electron transport layer 16, an electron injection layer 17, and a cathode 18.

Figure 8:
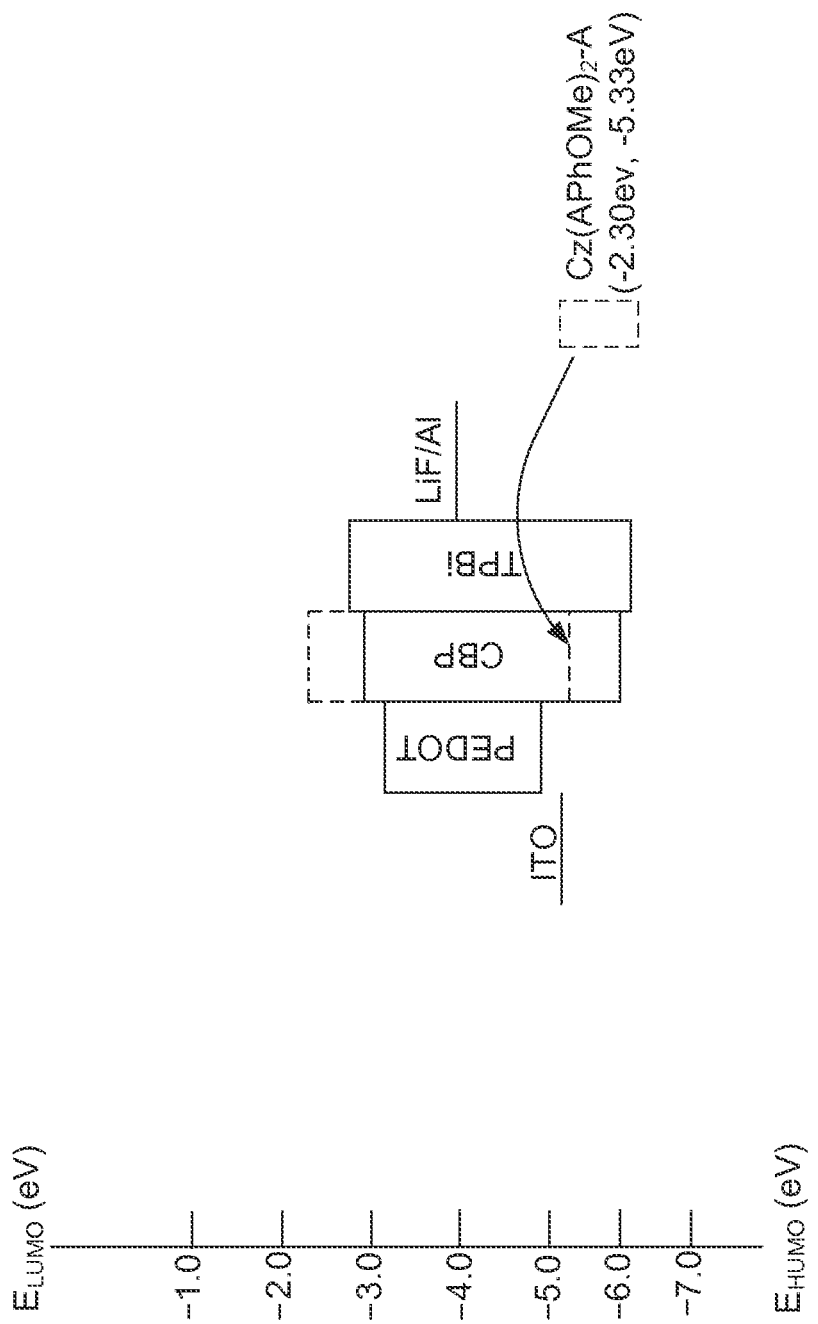
FIG. 8 shows a first energy band diagram of the OLED shown by FIG. 7.

Continuously referring to FIG. 7, and simultaneously refer to FIG. 8, there is shown a first energy band diagram of the OLED shown by FIG. 7. For the OLED 1 having the first energy band diagram, In the OLED 1, indium tin oxide (ITO) substrate, lithium fluorine (LiF), and aluminum (Al) are respectively used as the anode 11, the electron injection layer 17 and the cathode 18. In addition, the hole injection layer 12 is made of poly(3,4-ethylenedioxythiophene)polystyrene sulfonate (PEDOT:PSS) and the electron transport layer 16 is formed by using 1,3,5-tris(N-phenylbenzimidazol-2-yl)benzene (TPBi) as the manufacturing material. Moreover, 4,4'-Bis(9H-carbazol-9-yl)biphenyl (CBP) and Cz(APhOMe)$_2$-A are used for being the host light-emitting layer 14 and the guest light-emitting material 15 (i.e., guest dye).

Figure 9:
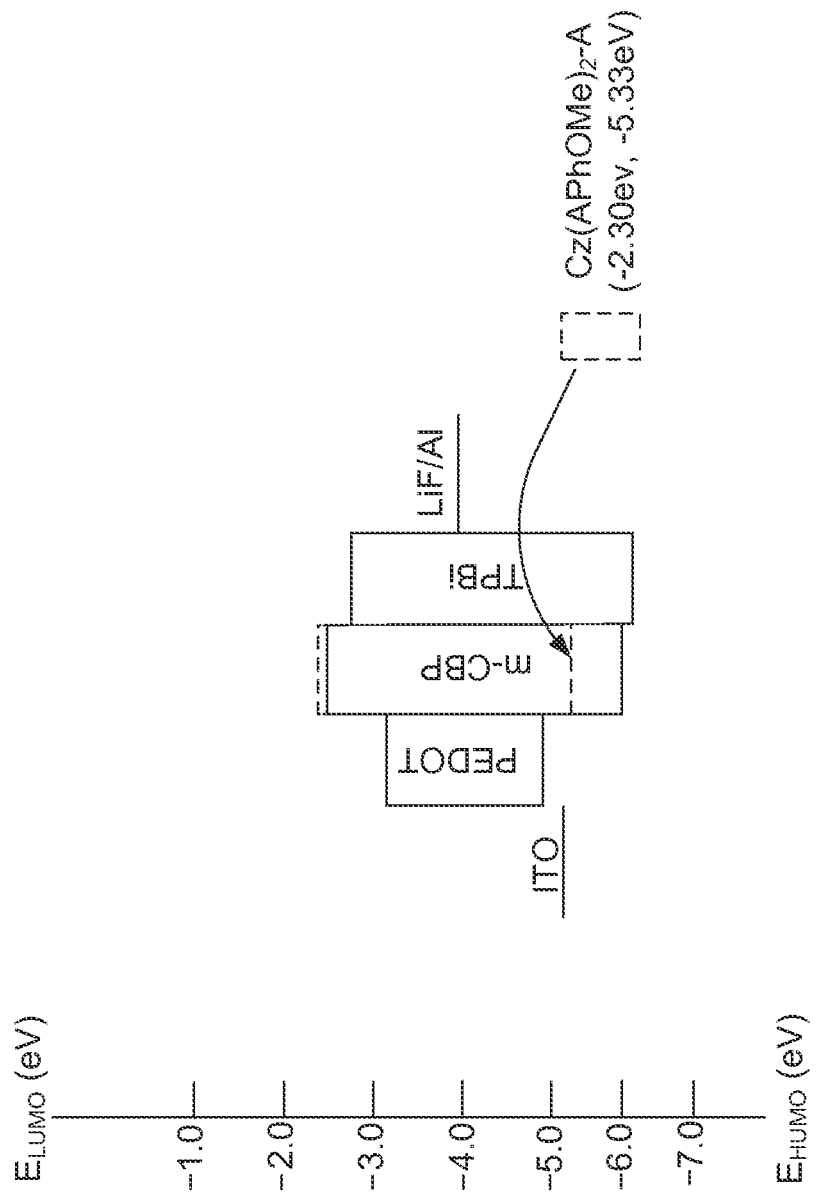
FIG. 9 shows a second energy band diagram of the OLED shown by FIG. 7.

Referring to FIG. 7 again, and simultaneously refer to FIG. 9, there is shown a second energy band diagram of the OLED shown by FIG. 7. For the OLED 1 having the second energy band diagram, In the OLED 1, indium tin oxide (ITO) substrate, lithium fluorine (LiF), and aluminum (Al) are respectively used as the anode 11, the electron injection layer 17 and the cathode 18. In addition, the hole injection layer 12 is made of poly(3,4-ethylenedioxythiophene)polystyrene sulfonate (PEDOT:PSS) and the electron transport layer 16 is formed by using 1,3,5-tris(N-phenylbenzimidazol-2-yl)benzene (TPBi) as the manufacturing material. Moreover, 3,3'-bis(carbazol-9-yl)biphenyl (mCBP) and Cz(APhOMe)$_2$-A are used for being the host light-emitting layer 14 and the guest light-emitting material 15.

The measurement data of the two OLEDs have been obtained and recorded in table 2 presented as the diagram shown in FIG. 10. The measurement data includes doping concentration, operating voltage (OV), external quantum efficiency (EQE), CIE color coordinates, and peak wavelength of emission spectrum (EL$_{max}$). Moreover, please simultaneously refer to FIG. 11, which illustrate an emission spectrum diagram of the OLED using CBP as the host light-emitting layer and the OLED using mCBP as the host light-emitting layer.

Figure 11:
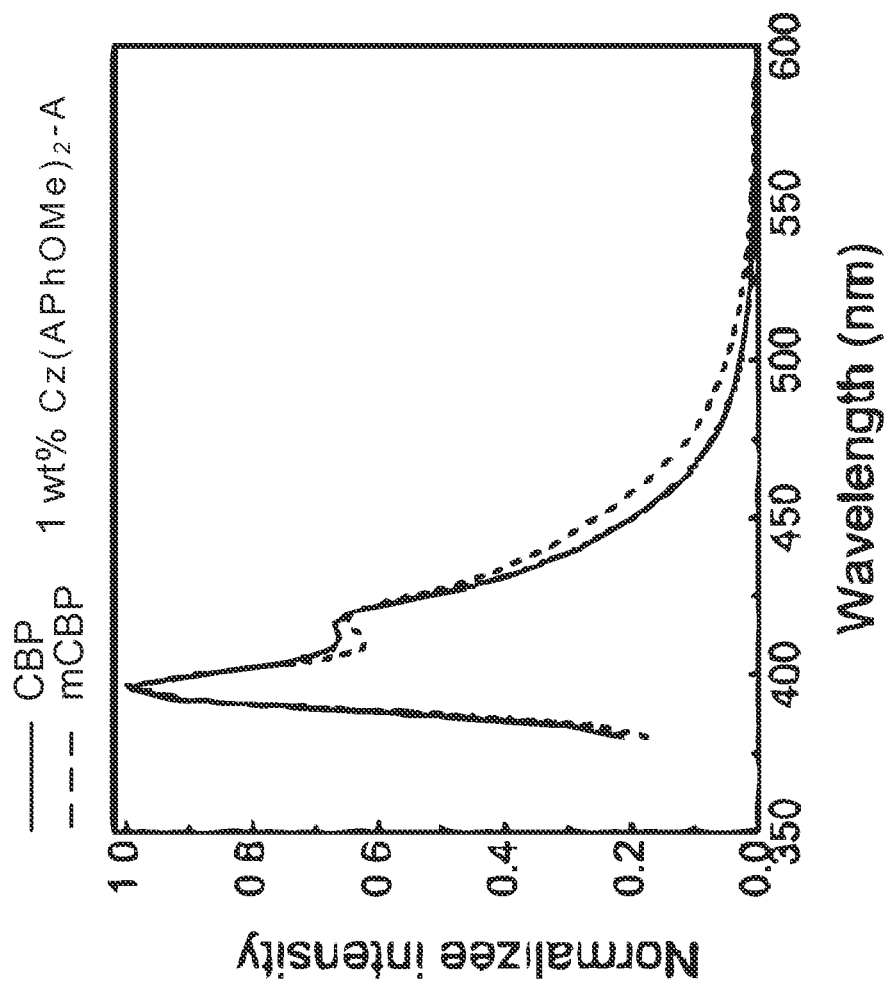
FIG. 11 shows an emission spectrum diagram of the OLED using CBP as the host light-emitting layer and the OLED using mCBP as the host light-emitting layer.
Figure 12:
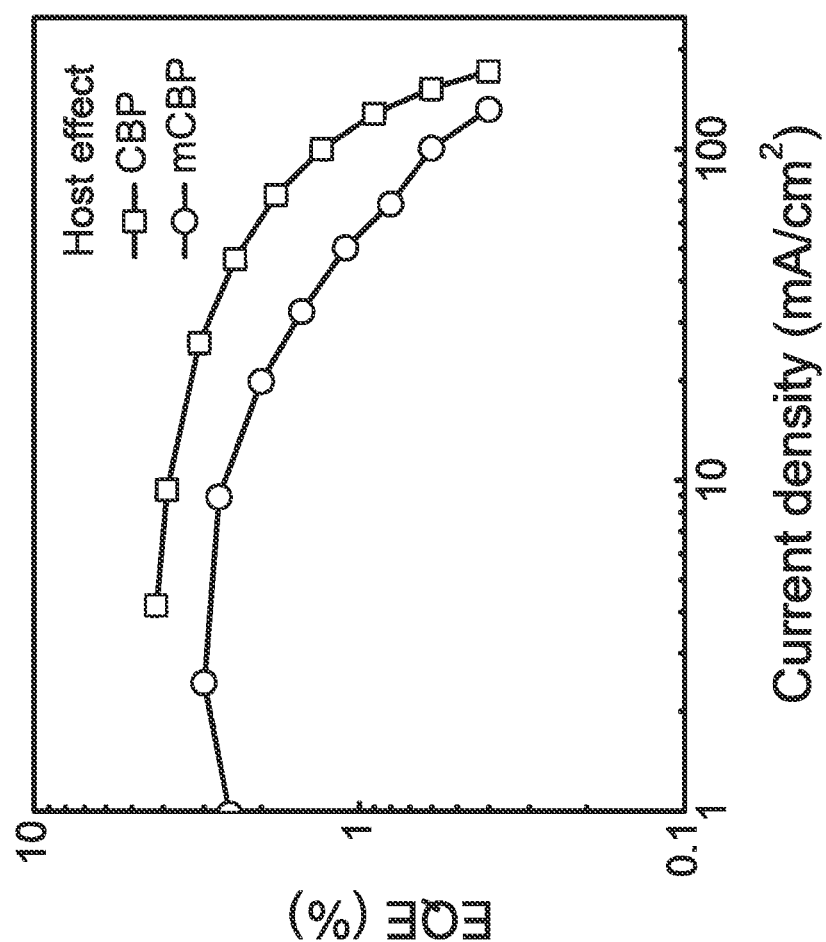
FIG. 12 is a data plot of EQE versus current density.

From table 2 and FIG. 11, it can find that the UV light, no matter emitted by the OLED 1 using CBP material as the host light emitting layer 14 or using mCBP material as the host light emitting layer 14, has shown the pure UV emission with a peak wavelength of 396 nm and 392, respectively. That is, both the CBP and the mCBP can be used as a host light emitting material when manufacturing a ultra-violet OLED using the Cz(APhOMe)$_2$-A as the guest light emitting material. Furthermore, according to table 2 and the data plot of EQE versus current density shown by FIG. 12, it can find that the OLED using the Cz(APhOMe)$_2$-A as the guest dye and the CBP as the host light emitting material performs better EQE comparing to the OLED using the Cz(APhOMe)$_2$-A as the guest dye and the mCBP as the host light emitting material. That is, there is a host effect produced by the CBP and mCBP to the Cz(APhOMe)$_2$-A.

Therefore, through above descriptions, the novel electro-fluorescent emitter for ultra-violet OLED proposed by the present invention has been introduced completely and clearly; in summary, the present invention includes the advantages of:

(1) The electro-fluorescent emitter is a ultra-violet fluorescent emitting material including a high quantum yield of ~78%, which can be doped into a host light-emitting layer of an organic light emitting diode (OLED) for being a guest light-emitting material, so as to facilitate the OLED be able to emit a UV light belong to the near-UV region with a high external quantum efficiency.

(2) Moreover, the experiment results also proved that the UV light emitted by the OLED using this electro-fluorescent emitter as the guest light emitting material is a pure UV light without including any visible light component and/or an infrared ray component; so that, this pure UV light can be applied in the technique fields of biological and chemical sensors, leakage detection in automobiles, high density information storage devices, water treatment for germicidal protection, crack detection in airplanes, forensic investigations, sanitation and sterilization, laboratory researches, food industries, and fraud detection.

The above description is made on embodiments of the present invention. However, the embodiments are not intended to limit scope of the present invention, and all equivalent implementations or alterations within the spirit of the present invention still fall within the scope of the present invention.

What is claimed is:

1. An electro-fluorescent emitter for ultra-violet OLED, wherein the electro-fluorescent emitter is a ultra-violet fluorescent emitting material constructed by at least one polycyclic aromatic hydrocarbons (PAHs) and at least one benzene compound through a Sonogashira coupling reaction by using a plurality of catalytic agents comprising Pd(PPh$_3$)$_2$Cl$_2$) (Palladium(II)bis(triphenylphosphine)dichloride), PPh$_3$ (Triphenylphosphine), CuI (Cuprous iodide), and (C$_2$H$_5$)$_3$N (Triethylamine); wherein the chemical structure of the ultra-violet fluorescent emitting material being represented by following formulae 4 or 5:

Formula 4

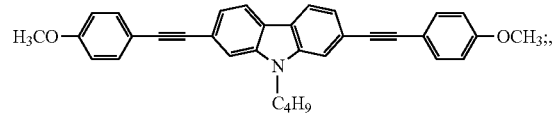

Formula 5

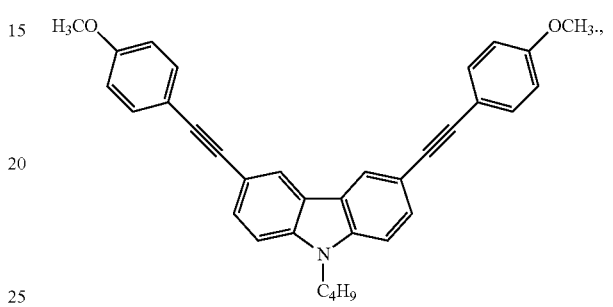

2. The electro-fluorescent emitter of claim 1, wherein the chemical structure of the polycyclic aromatic hydrocarbons is represented by following formulae 1 or 2:

Formula 1

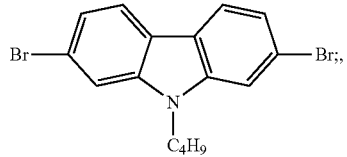

Formula 2

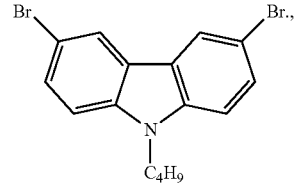

3. The electro-fluorescent emitter of claim 1, wherein the chemical structure of the benzene compound is represented by following formula 3:

Formula 3

4. The electro-fluorescent emitter of claim 1, wherein the ultra-violet fluorescent emitting material represented by the formulae 4 or 5 has a high occupied molecular orbital energy level (EHOMO) ranging from −5.41 eV to −5.53 eV and a lowest unoccupied molecular orbital energy level (ELUMO) ranging from −2.03 eV to −2.30 eV.

5. The electro-fluorescent emitter of claim 1, wherein the formed ultra-violet fluorescent emitting material can be doped into a host light-emitting layer of an organic light emitting diode (OLED) for being a guest light-emitting material.

* * * * *